(12) United States Patent
Benz et al.

(10) Patent No.: US 12,422,125 B2
(45) Date of Patent: Sep. 23, 2025

(54) SHAPED PART AND INFORMATION DISPLAY SYSTEM

(71) Applicant: Novem Car Interior Design GmbH, Vorbach (DE)

(72) Inventors: Diana Benz, Weiden i.d. Opf (DE); Vanessa Mai, Heinersreuth (DE); Andreas Karl, Speinshart (DE); Rainer Merkl, Kemnath (DE)

(73) Assignee: Novem Car Interior Design GmbH (DE)

( * ) Notice: Subject to any disclaimer, the term of this patent is extended or adjusted under 35 U.S.C. 154(b) by 0 days.

(21) Appl. No.: 18/647,986

(22) Filed: Apr. 26, 2024

(65) Prior Publication Data

US 2025/0060084 A1     Feb. 20, 2025

(30) Foreign Application Priority Data

May 15, 2023    (DE) .......................... 102023112781.0

(51) Int. Cl.
    *F21V 9/32*         (2018.01)
    *H05K 5/02*         (2006.01)

(52) U.S. Cl.
    CPC ................. *F21V 9/32* (2018.02); *H05K 5/02* (2013.01)

(58) Field of Classification Search
    CPC .. F21V 9/32; H05K 5/02; B60R 13/02; B60R 21/045; B60R 7/06; B60R 7/04; B32B 2451/00
    See application file for complete search history.

(56) References Cited

U.S. PATENT DOCUMENTS

| | | | |
|---|---|---|---|
| 6,596,416 B2* | 7/2003 | Nelson | .................... B32B 27/04 |
| | | | 428/322.2 |
| 2014/0264079 A1* | 9/2014 | Tarahomi | ............... C09K 11/08 |
| | | | 252/301.36 |

(Continued)

FOREIGN PATENT DOCUMENTS

| | | |
|---|---|---|
| CN | 115366810 A * | 11/2022 |
| DE | 102006036062 A1 | 2/2008 |

(Continued)

OTHER PUBLICATIONS

Wang et al. CN 115366810 A, Machine Translation Nov. 22, 2022.*

*Primary Examiner* — Tracie Y Green
(74) *Attorney, Agent, or Firm* — Workman Nydegger

(57) ABSTRACT

A shaped part includes a decorative layer with a front side designed as a visible side and a back side opposite the front side, and a carrier arranged on the back side of the decorative layer, wherein a transparent or translucent top layer is arranged on the front side of the decorative layer. The invention is characterized in that a UV-activatable phosphorescent additive is applied to the front side of the top layer and/or is at least partially incorporated into the top layer in a designated phosphorescent region, wherein the phosphorescent additive can be excited or is excitable by a UV illumination source to emit light in the visible range, and wherein the phosphorescent additive is applied to the front side of the top layer or is incorporated into the decorative layer in such a way that the phosphorescent additive forms a luminous phosphorescent symbol in the excited state.

8 Claims, 1 Drawing Sheet

(56) References Cited

U.S. PATENT DOCUMENTS

| | | | | |
|---|---|---|---|---|
| 2016/0193763 A1* | 7/2016 | Egerer | .............. | B29C 45/14508 |
| | | | | 428/61 |
| 2024/0295687 A1* | 9/2024 | Martin | .................... | B60R 13/02 |
| 2024/0316899 A1* | 9/2024 | Martin | .................. | F21V 14/003 |

FOREIGN PATENT DOCUMENTS

| | | |
|---|---|---|
| DE | 202017007050 U1 | 4/2019 |
| EP | 2060444 A1 | 5/2009 |

* cited by examiner

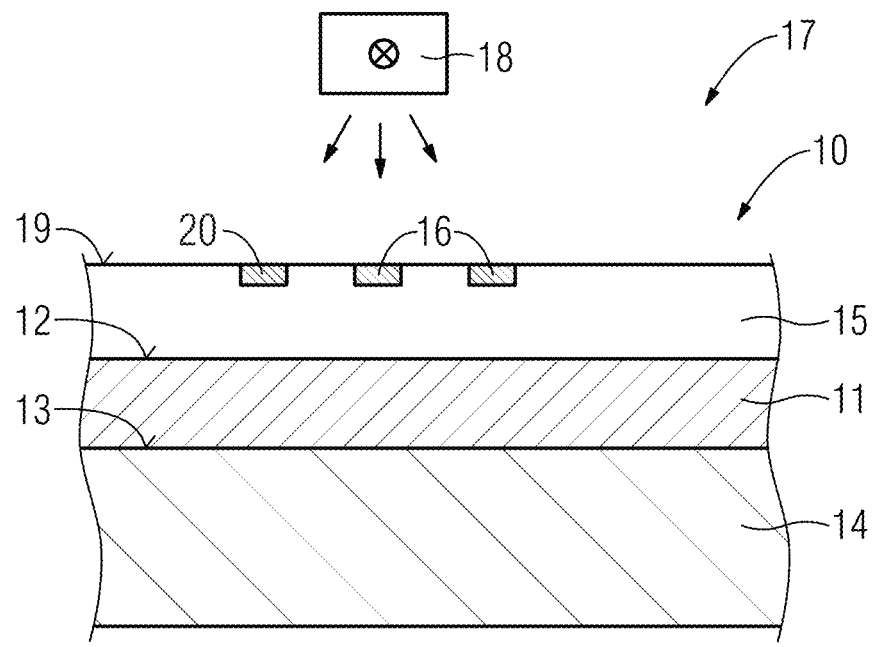

SHAPED PART AND INFORMATION DISPLAY SYSTEM

CROSS-REFERENCE TO RELATED APPLICATIONS

The present invention claims priority to German Application 102023112781.0, filed on May 15, 2023. The entire content of each of the aforementioned patent applications is incorporated herein by reference.

BACKGROUND OF THE INVENTION

1. Field of the Invention

The invention relates to a shaped part, in particular a decorative part (also: body trim part) and/or panel part designed as a shaped part for a vehicle interior. The invention further relates to an information display system.

2. The Relevant Technology

Numerous decorative and panel parts are installed in the vehicle interior, for example door panels, console panels, and instrument panels. The decorative and panel parts also include control buttons and their covers.

UV radiation can be used to clean vehicle interiors, since it kills viruses and bacteria. UV light is not visible to the human eye, but it is harmful. Thus, there is a need to inform vehicle occupants that the vehicle interior has recently been cleaned by means of UV radiation. Furthermore, there is a desire to alert vehicle occupants who are present during UV cleaning inside the vehicle interior to the non-visible but existing potential health hazard posed by UV light.

BRIEF SUMMARY OF THE INVENTION

The object of the invention is to provide a new shaped part and a new information display system, in particular a new shaped part and a new information display system with which vehicle occupants are informed that the vehicle interior has been cleaned by means of UV radiation and/or are warned of a danger due to UV radiation.

This object is achieved by a shaped part with the features of claim 1 and an information display system with the features of claim 5. Advantageous embodiments and further developments are provided in each of the dependent claims.

The shaped part according to the invention comprises a decorative layer with a front side designed as a visible side and a back side opposite the front side, and a carrier arranged on the back side of the decorative layer, wherein a transparent or translucent top layer is arranged on the front side of the decorative layer.

The invention is characterized in that a UV-activatable phosphorescent additive is applied to the front side of the top layer and/or is at least partially incorporated into the top layer in a designated phosphorescent region, wherein the phosphorescent additive can be excited or is excitable by a UV illumination source to emit light in the visible range, and wherein the phosphorescent additive is applied to the front side of the top layer or is incorporated into the decorative layer in such a way that the phosphorescent additive forms a luminous phosphorescent symbol in the excited state, in particular when viewed from above on the visible side of the shaped part.

Phosphorescence is a form of luminescence. With luminescence, a physical system is put into an excited state by externally supplied energy, for example irradiation with UV radiation, and emits light in the visible range during the transition to its ground state; the luminescent material lights up. A distinction is made between fluorescence and phosphorescence. With fluorescence, the glow subsides quickly after the end of UV irradiation, usually within a millionth of a second; i.e., for an observer, the glow disappears immediately after the UV illumination source is switched off. With phosphorescence, on the other hand, there is an afterglow that can last for several hours. For an observer, phosphorescent materials thus continue to glow for several hours even after the UV illumination source has been switched off.

The phosphorescent symbol can, for example, be a cleaning message, such as the writing "Clean" and/or "Antimicrobial" and/or "Antiviral" and/or "Cleaned" and/or a cleaning logo and/or a cleaning pictogram, and/or a warning symbol, such as an exclamation mark in a triangle or a symbol that indicates radiation, or even a writing such as "Caution," "Caution: UV radiation" or "UV radiation."

Thus, the advantages of the invention lie in particular in the fact that, even after the UV illumination source has been switched off, a vehicle occupant is informed about the cleaning of the vehicle interior by means of UV radiation and thus the cleaning status of the vehicle by the afterglow of the phosphorescent symbol for a prolonged period of time. Furthermore, through the lighting up of phosphorescence symbol during cleaning by means of UV radiation, the user is alerted to a possible hazard from UV radiation. A further advantage of the invention is that it is a so-called "hidden til lit" solution. This means that a few hours after switching off the UV illumination source, when the cleaning status is no longer displayed and there is no hazard from UV radiation, the vehicle occupants will not be able to see any phosphorescent symbols, such as cleaning and/or warning symbols, which may have a negative visual impact on the design. However, if UV radiation hits the symbol formed by the additive, it lights up. A further advantage is that the solution according to the invention can be easily integrated into a wide range of existing shaped parts.

The phosphorescent additive can be applied to the top layer or incorporated into the top layer by means of a screen printing process and/or filler process and/or embossing process.

Preferably, the top layer is a lacquer layer or film, in particular a transparent or translucent one.

A further development of the invention provides that, in addition to the UV-activatable phosphorescence additive, a UV-activatable fluorescence additive is applied to the front side of the top layer and/or at least partially incorporated into the top layer in a designated fluorescence region, wherein the fluorescent additive can also be excited or is excitable by the UV illumination source to emit light in the visible range, and wherein the fluorescent additive is applied to the front side of the top layer or is incorporated into the decorative layer in such a way that the fluorescent additive forms a luminous fluorescent symbol in the excited state.

This further development combines the advantage of phosphorescence, the afterglow, with the advantage of fluorescence, the immediate extinguishing of the glow for the observer when the UV illumination source is switched off. The fluorescent symbol alerts the vehicle occupants to a current potential hazard from the active UV illumination source, while the phosphorescent symbol indicates the cleaning status even after the UV illumination source has been switched off. If the fluorescent symbol and phosphorescent symbol light up, the vehicle occupant is alerted to the possible hazard from UV radiation. However, if only the phosphorescent symbol lights up, the vehicle occupant is alerted that the vehicle interior has already been cleaned by UV radiation. If neither the fluorescent symbol nor the phosphorescent symbol lights up, the vehicle occupant receives no indication of the cleaning status or of a possible hazard from UV radiation and thus knows that the UV illumination source is currently switched off and that no cleaning by means of UV radiation has taken place in the last few hours.

The fluorescent symbol can be a warning symbol, such as an exclamation mark in a triangle or a symbol that indicates radiation, or even writing such as "Caution," "Caution: UV radiation" or "UV radiation."

The fluorescent additive can also be applied to the top layer or incorporated into the top layer by means of a screen printing process and/or filler process and/or embossing process.

The information display system according to the invention, in particular for the vehicle interior, comprises a UV illumination source and a shaped part. The shaped part comprises a decorative layer with a front side designed as a visible side and a back side opposite the front side, and a carrier arranged on the back side of the decorative layer, wherein a transparent or translucent top layer is arranged on the front side of the decorative layer.

The information display system according to the invention is characterized in that a UV-activatable phosphorescent additive is applied to the front side of the top layer of the shaped part in a designated phosphorescent region and/or is at least partially incorporated into the top layer, wherein the phosphorescent additive can be excited is excitable by the UV illumination source to emit light in the visible range, and wherein the phosphorescent additive is applied to the front side of the top layer or is incorporated into the decorative layer in such a way that the phosphorescent additive forms a luminous phosphorescent symbol in the excited state.

Further embodiments with regard to the shaped part of the information display system and the advantages also with regard to the information display system result from the above explanations regarding the shaped part according to the invention.

The phosphorescent additive can be applied to the top layer or incorporated into the top layer by means of a screen printing process and/or filler process and/or embossing process.

Preferably, the top layer is a lacquer layer or film, in particular a transparent or translucent one.

A further development of the information display system provides that, in addition to the UV-activatable phosphorescence additive, a UV-activatable fluorescence additive is applied to the front side of the top layer of the shaped part and/or is at least partially incorporated into the top layer of the shaped part in a designated fluorescence region, wherein the fluorescent additive can be excited or is excitable by the UV illumination source to emit light in the visible range, and wherein the fluorescent additive is applied to the front side of the top layer or is incorporated into the decorative layer in such a way that the fluorescent additive forms a luminous fluorescent symbol in the excited state.

Further embodiments with regard to this further development and its advantages can also be seen from the above explanations regarding the shaped part according to the invention.

The fluorescent additive can also be applied to the top layer or incorporated into the top layer by means of a screen printing process and/or filler process and/or embossing process.

In particular, the UV illumination source is spaced from the shaped part. The UV illumination source can be located centrally in the vehicle, whereas the shaped part can be installed in the region of the dashboard or the door panels, for example. Preferably, the UV illumination source is aligned in such a way that UV light emitted from the UV illumination source radiates in the direction of the phosphorescence region on or in the top layer in which the phosphorescent additive is provided. With a corresponding embodiment of the shaped part, the UV illumination source is also preferably aligned in such a way that UV light emitted by the UV illumination source also radiates in the direction of the fluorescence region on or in the top layer in which the fluorescent additive is provided. In embodiments, the UV illumination unit can be coupled with a locking and/or unlocking of the vehicle, for example by switching on the UV illumination unit when the vehicle is locked and/or switching off the UV illumination unit when the vehicle is unlocked.

BRIEF DESCRIPTION OF THE DRAWINGS

FIG. 1 illustrates a schematic drawing of an information display system in accordance with an implementation of the present invention.

DETAILED DESCRIPTION

The invention is explained in more detail below also with regard to further features and advantages on the basis of the description of an exemplary embodiment and with reference to the accompanying schematic drawing. The only FIGURE shows an information display system 17 according to the invention with a UV illumination source 18 and a shaped part 10 according to the invention, wherein, for the shaped part 10, only a section of a schematic cross-sectional view is shown.

The information display system 17 according to the invention is provided for a vehicle interior and comprises a UV illumination source 18 and a shaped part 10 designed as a decorative and/or panel part for the vehicle interior. The UV illumination source 18 is arranged centrally in the vehicle, whereas the shaped part 10 can be installed in the region of the dashboard or the door panels, for example.

According to the exemplary embodiment, the shaped part 10 according to the invention comprises a decorative layer 11 with a front side 12 designed as a visible side and a back side 13 opposite the front side 12, and a carrier 14 arranged on the back side 13 of the decorative layer 11. However, one or more further layers or intermediate layers can also be arranged between the decorative layer 11 and the carrier 14.

A transparent or translucent top layer 15 is arranged on the front side 12 of the decorative layer 11. According to the exemplary embodiment, the top layer 15 is a lacquer layer.

A UV-activatable phosphorescent additive 16 is applied in a designated phosphorescent region on the front side 19 of the top layer 15, wherein the phosphorescent additive 16 can be excited by the UV illumination source 18 to emit light in the visible range. In addition, in embodiments, a UV-activatable fluorescent additive 20 can be applied to the front surface 19 of the top layer 15 in a similar manner (not shown). The phosphorescent additive 16 is also applied to the front side 19 of the top layer 15 in such a way that it forms a phosphorescent symbol in the excited state, i.e., a phosphorescent symbol lights up on or in the top layer 15 in the excited state. In particular, the phosphorescent symbol is a cleaning and/or warning message, for example, a writing on the cleaning status and/or a warning sign or a writing that alerts the vehicle occupants to the activated UV illumination source and thus to the danger of UV light, which can be harmful to the human eye.

The phosphorescent additive 16 can be applied to the top layer 15 or incorporated into the top layer 15 by means of a screen printing process, filler process or embossing process.

The UV illumination source 18 is aligned in such a way that UV light emitted from the UV illumination source 18 radiates in the direction of the phosphorescent region on or in the top layer 15 in which the phosphorescent additive 16 is provided.

LIST OF REFERENCE SIGNS

10 Shaped part
11 Decorative layer
12 Front side (decorative layer)
13 Rear side (decorative layer)
14 Carrier
15 Top layer
16 Phosphorescent additive
17 Information display system
18 UV illumination source
19 Front side (top layer)

We claim:

1. A shaped part comprising
a decorative layer with a front side designed as a visible side and a back side opposite the front side, and a carrier arranged on the back side of the decorative layer,
wherein a transparent or translucent top layer is arranged on the front side of the decorative layer,
wherein a UV-activatable phosphorescent additive is applied to the front side of the top layer or is incorporated into the top layer,
wherein the phosphorescent additive can be excited or is excitable by a UV illumination source to emit light in the visible range,
wherein the phosphorescent additive is applied to the front side of the top layer or is incorporated into the top layer in such a way that the phosphorescent additive forms a luminous phosphorescent symbol in the excited state,
wherein, in addition, a UV-activatable fluorescent additive is applied to the front side of the top layer or is incorporated into the top layer,
wherein the fluorescent additive can also be exited or is excitable by the UV illumination source to emit light in the visible range, and
wherein the fluorescent additive is applied to the front side of the top layer or is incorporated into the top layer in such a way that the fluorescent additive forms a luminous fluorescent symbol in the excited state.

2. The shaped part according to claim 1,
wherein:
the phosphorescent additive is applied to the top layer or is incorporated into the top layer by means of a screen printing process and/or filler process and/or embossing process.

3. The shaped part according to claim 1,
wherein:
the top layer is a lacquer layer or film.

4. An information display system comprising
a UV illumination source and a shaped part,
wherein the shaped part comprises a decorative layer with a front side designed as a visible side and a back side opposite the front side, and a carrier arranged on the back side of the decorative layer,
wherein a transparent or translucent top layer is arranged on the front side of the decorative layer,
wherein a UV-activatable phosphorescent additive is applied to the front side of the top layer of the shaped part or is incorporated into the top layer of the shaped part,
wherein the phosphorescent additive can be excited or is excitable by the UV illumination source to emit light in the visible range,
wherein the phosphorescent additive is applied to the front side of the top layer or is incorporated into the top layer in such a way that the phosphorescent additive forms a luminous phosphorescent symbol in the excited state
wherein, in addition, a UV-activatable fluorescent additive is applied to the front side of the top layer or is incorporated into the top layer,
wherein the fluorescent additive can also be exited or is excitable by the UV illumination source to emit light in the visible range, and
wherein the fluorescent additive is applied to the front side of the top layer or is incorporated into the top layer in such a way that the fluorescent additive forms a luminous fluorescent symbol in the excited state.

5. The information display system according to claim 4,
wherein:
the phosphorescent additive is applied to the top layer or is incorporated into the top layer by means of a screen printing process and/or filler process and/or embossing process.

6. The information display system according to claim 4,
wherein:
the top layer is a lacquer layer or film.

7. The information display system according to claim 4,
wherein:
the UV illumination source is spaced from the shaped part.

8. The information display system according to claim 4,
wherein:
the UV illumination source is aligned in such a way that UV light emitted from the UV illumination source radiates in the direction of the phosphorescence region on or in the top layer in which the phosphorescent additive is provided.

* * * * *